Figure 1:
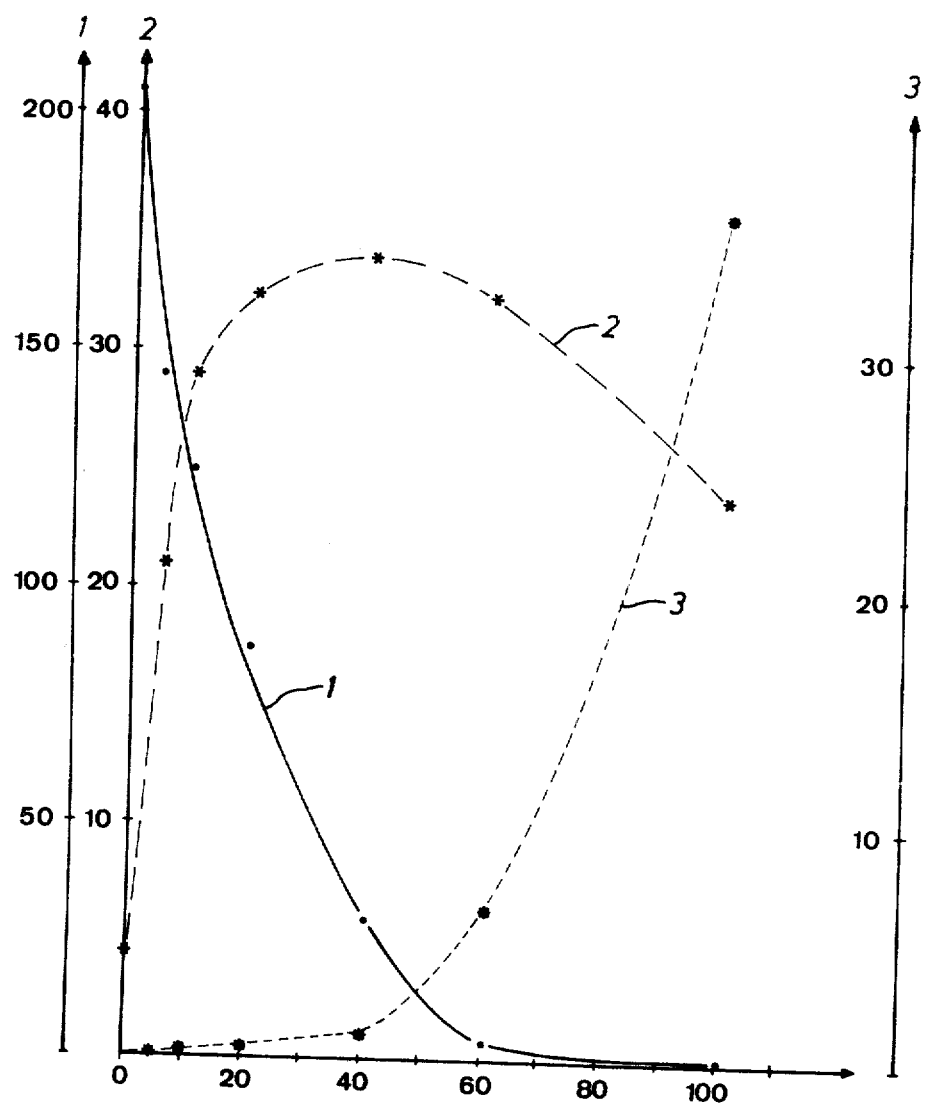

United States Patent [19]

Frommer et al.

[11] 3,934,006

[45] Jan. 20, 1976

[54] PHARMACEUTICAL COMPOSITIONS COMPRISING SACCHARASE INHIBITORS

[75] Inventors: Werner Frommer; Walter Puls; Delf Schmidt, all of Wuppertal, Germany

[73] Assignee: Bayer Aktiengesellschaft, Leverkusen, Germany

[22] Filed: June 24, 1974

[21] Appl. No.: 482,661

Related U.S. Application Data

[62] Division of Ser. No. 336,720, Feb. 28, 1973, Pat. No. 3,879,546.

[30] Foreign Application Priority Data

Mar. 1, 1972  Germany............................ 2209832

[52] U.S. Cl. ............................................... 424/115
[51] Int. Cl.² ......................................... A61K 27/00
[58] Field of Search .................................... 424/115

[56] References Cited

UNITED STATES PATENTS 3,806,421  4/1974  Ueda et al. ................. 424/115 X

*Primary Examiner*—Frederick E. Waddell
*Attorney, Agent, or Firm*—Depaoli & O'Brien

[57] ABSTRACT

This invention relates to the production of saccharase inhibitors in which a polysaccharidic or oligosaccharidic amylase inhibitor is hydrolytically degraded either enzymatically or by acid hydrolysis. The invention also relates to the use of said saccharase inhibitors in pharmaceutically acceptable therapeutic compositions in the treatment of conditions indicating adiposity, hyperlipaemia (atherosclerosis), diabetes, prediabetes, caries and the like.

6 Claims, 3 Drawing Figures

3,934,006

PHARMACEUTICAL COMPOSITIONS COMPRISING SACCHARASE INHIBITORS

This is a division of application Ser. No. 336,720, filed Feb. 28, 1973, now U.S. Pat. No. 3,879,546.

BACKGROUND OF THE INVENTION

Polysaccharidic or oligosaccharidic amylase inhibitors which are the starting materials employed in the instant invention are formed from *actinomycetes*. These inhibitors are formed by microorganisms of the order Actinomycetales, especially by those of the family of Streptomycetaceae, Thermoactinomycetaceae, Micromonosporaceae, Nocardiaceae and above all those of the family Actinoplanaceae. They are also formed to a particularly high degree by strains of the genera Actinoplanes, Ampullariella, Streptosporangium, Streptomyces, Chainia, Pilimelia, Planomonospora, and Actinobifida.

The polysaccharidic or oligosaccharidic amylase inhibitors are generally prepared by culturing a microbe of the order Actinomycetales and extracting the inhibitor from the resultant culture.

The preferred microorganisms are preferably of the family Streptomycetaceae or Actinoplanaceae. Particularly preferred microorganisms are strains of Actinoplanaceae, CBS 961.70, 615.71, 614.71, and 957.70.

Strains of the order Actinomycetales, especially those of the families Streptomycetaceae and Actinoplanaceae, are isolated in a known manner from samples of soil or strains of the order bought from culture collections. Culture flasks containing nutrient solutions which permit the growth of these strains are inoculated with inoculum of these strains. For example, the glycerine-glycine nutrient solution according to von Plotho, of composition 2% glycerine, 0.25% glycine, 0.1% NaCl, 0.1% $K_2HPO_4$ 0.01% $FeSO_4 . 7 H_2O$, 0.01% $MgSO_4 . 7 H_2O$ and 0.1% $CaCO_3$ can be used. For more rapid growth, it is advisable also to add to such a nutrient solution complex sources of carbon, such as, for example, corn-steep liquor or soya flour or yeast extract or protein hydrolysates, for example NZ-amines, or mixtures of these substances. In these cases, the pH value of the solution must be adjusted. An initial pH of the nutrient solution of between 6.0 and 8.0, especially between 6.5 and 7.5, is preferred.

The glycerine of the nutrient solution can also be replaced by other sources of carbon, such as, for example, glucose or sucrose or starch or mixtures of these substances. Instead of glycine, it is also possible to use other sources of nitrogen, such as, for example, yeast extract, soya flour, NZ-amines, pharmamedia and others. The concentrations of the sources of carbon and nitrogen, and also the concentrations of the salts, can vary within wide limits. $FeSO_4$, $CaCO_3$ and $MgSO_4$ can also be entirely absent. 100–200 ml, for example, of the nutrient solution are introduced into 1 liter Erlenmeyer flasks, sterilized in a known manner and inoculated with the strain to be investigated, and the flask is incubated on shaking machines at 15°14 60°C., preferably at 24°–50°C. If the culture shows growth, which generally takes place after 1–10 days, and in most cases after 3–5 days, a sample of, for example, 5 ml is taken and tested.

RELATIONSHIP TO COPENDING APPLICATIONS

Polysaccharidic or oligosaccharidic amylase inhibitors which can be used as starting materials for the instant invention are disclosed in U.S. Pat. No. 3,876,766.

Additional polysaccharidic or oligosaccharidic amylase inhibitors are disclosed in U.S. Pat. No. 3,855,066.

THE PRESENT INVENTION

Although polysaccharides or oligosaccharides or derivatives thereof are highly potent amylase inhibitors, they are only medium-strength or weak saccharase inhibitors. It has now been found that these materials can be converted into potent saccharase inhibitors by subjecting them to hydrolytic degradation. By the process of this invention their saccharase-inhibiting activity is greatly enhanced while a concurrent diminution of their amylase-inhibiting activity takes place so that the former predominates.

It is to be understood that in the specification and claims, the term "amylase inhibitor" refers to a substance for which the quotient (f) in the following formula is greater than 0.1

$$f = \frac{[SIU]}{[AIU]} \times 10^3$$

where SIU is equal to a saccharase inhibiting unit and AIU is equal to an amylase inhibiting unit.

The experimental methods for determining SIU and AIU, as well as the definitions thereof will now be described.

AMYLASE TEST

One amylase inhibitor unit (1 AIU) is defined as the amount of inhibitor which inhibits two amylase units to the extent of 50%. One amylase unit (AU) is the amount of enzyme which in 1 minute under the test conditions indicated below splits 1 $\mu$ equivalent of glucosidic bonds in starch. The $\mu$ equivalent of split bonds are determined colorimetrically with dinitrosalicylic acid as $\mu$ equivalent of reducing sugar formed and are quoted, with the aid of a maltose calibration curve, as $\mu$ equivalent maltose equivalents. To carry out the test, 0.1 ml of amylase solution (20-22 AU/ml) is mixed with 0 – 10 $\mu$ g of inhibitor or 0 – 20 $\mu$l of the solution to be tested in 0.4 ml of 0.02 M sodium glycerophosphate buffer/0.001 M $CaCl_2$, pH 6.9, and equilibrated in a water bath at 35°C for about 10–20 minutes. It is then incubated for 5 minutes at 35° C with 0.5 ml of a 1% strength starch solution (soluble starch of Messrs. Merck, Darmstadt, No. 1252) which has been prewarmed to 35°C, and is thereafter treated with 1 ml of dinitrosalicylic acid reagent (according to P. Bernfeld in Colowick-Kaplan, Meth. Enzymol., Volume 1, page 149). To develop the color, the batch is heated for five minutes on a boiling water bath and then cooled and treated with 10 ml of distilled water. The extinction at 540 nm is measured against a correspondingly made-up blank without amylase. For evaluation, the amylase activity which is still active after addition of inhibitor is read from a previously recorded amylase calibration curve, and the percentage inhibition of the amylase employed is calculated therefrom. The percentage inhibition is plotted as a function of the quotient:

$$\frac{\mu g \text{ of inhibitor}^*}{AU^{**}}$$

*relative to dry substance

**AU in the non-inhibited batch of the same series and the 50% inhibition point is read from the curve and converted to AIU/mg of inhibitor

SACCHARASE TEST

One saccharase inhibitor unit (SIU) is defined as the amount of inhibitor which inhibits two saccharase units to the extent of 50%. One saccharase unit (SU) is the amount of enzyme which in one minute, under the test conditions indicated below, splits 1 $\mu$ mol of saccharose into glucose and fructose. The $\mu$ mol of glucose formed is determined quantitatively by means of the glucose oxidase reaction under conditions under which a further splitting of the saccharose by the saccharase no longer takes place. To carry out the test, 0.05 ml of a saccharase solution[1] adjusted to 0.12 SU is mixed with 0 – 20 $\mu$g of inhibitor or 0 – 20 $\mu$l of the solution to be tested and made up to 0.1 ml with 0.1 M sodium maleate buffer of pH 6.0. The mixture is equilibrated for 10 minutes at 35°C and 0.1 ml of an 0.05 M saccharose solution in 0.1 M sodium maleate buffer of pH 6.0, which has been prewarmed to 35°C, is then added. The mixture is incubated for 20 minutes at 35°C and the saccharase reaction is stopped by adding 1 ml of glucose oxidase reagent[2] and incubated for a further 30 minutes at 35°C. Thereafter, 1 ml of 50% strength $H_2SO_4$ is added and the mixture is measured at 545 nm against a corresponding blank. For evaluation, the percentage inhibition of the saccharase employed is calculated and converted, from the 50% inhibition point with the aid of a glucose calibration curve, to SIU/g or SIU/liter.

, 1. Solubilized saccharase from the mucous membrane of the small intestine of pigs according to B. Borgstrom and A. Dahlquist, Acta Chen. Scand. 12, (1958), page 1997. Diluted to an appropriate SU content with 0.1 M sodium maleate buffer at pH 6.0.

, 2. The glucose oxidase reagent is prepared by dissolving 2 mg of glucose oxidase (Messrs. Boehringer, No. 15,423 EGAB) in 100 ml of 0.565 M tris-HCl-buffer of pH 7.0 and subsequently adding 1 ml of detergent solution (2 g of Triton X 100 + 8 g of 95% ethanol, analytical grade). 1 ml of dianisidine solution (260 mg of odianisidine .2 HCl in 20 ml of $H_2O$) and 0.5 ml of 0.1% strength aqueous peroxidase solution (Messrs. Boehringer, No. 15,302 EPAP).

The conversion of the amylase inhibitors into saccharase inhibitors by hydrolytic degradation according to the invention involves splitting-off non-inhibiting molecular fragments (mostly monosaccharides, disaccharides or trisaccharides) from the inhibitor molecules.

As stated above this splitting-off of non-inhibiting molecule fragments is preferably effected either by enzymatichydrolytic or by chemical-hydrolytic splitting; preferably, acid hydrolysis at high temperatures is employed. Such hydrolysis is according to the invention generally carried out as follows. A 1 – 40% strength, preferably 2–20% strength, solution of the above-mentioned amylase inhibitor is hydrolyzed in 0.1 – 5 N, preferably 0.5 – 2N, Mineral acid, preferably HCl or $H_2SO_4$, for 0.1 – 6 hours, preferably for 0.5 – 4 hours, at 60°– 110°C, preferably 80°– 100°C.

As the hydrolysis proceeds, a steep drop in the amylase-inhibiting activity of the solution is observed, with a simultaneous steep rise and subsequent linear drop of the saccharase-inhibiting activity of the solutions. The quotient $$f = \frac{|SIU|}{|AIU|} \times 10^3$$

rises correspondingly steeply with increasing duration of hydrolysis. This is illustrated in FIG. 1, which shows the time course of the amylase inhibitor content (1), saccharase inhibitor content (2) and the quotient $f$ (3) of a 2% strength solution of the amylase inhibitor from the Strain CBS 961.70 on hydrolysis in 0.5 N HCl at 100°C over the course of 0 – 100 minutes. The time in minutes is plotted on the $-$ x-axis, AIU $\times$ 10$^6$ per liter is plotted on the $y_1$ axis, SIU $\times$ 10$^3$ per liter is plotted on the $y_2$ axis and the quotient $f$ is plotted on the $y_3$ axis.

Figure 2:
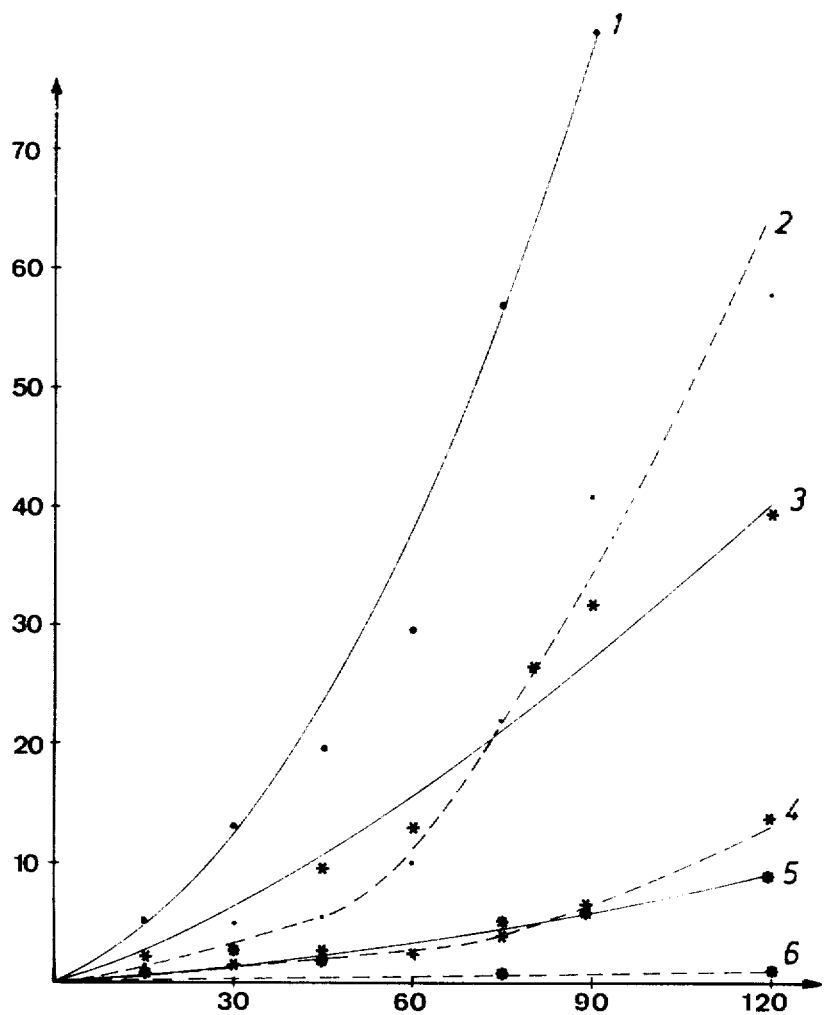
Figure 3:
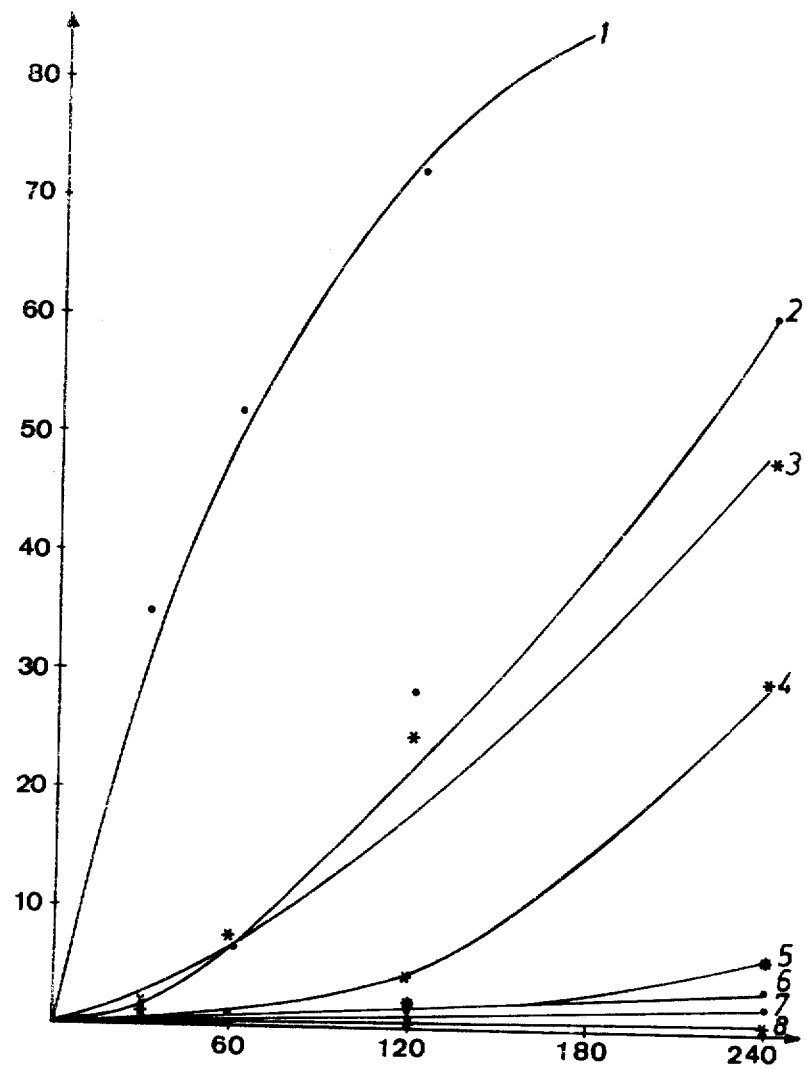

High acid concentration, low concentration of the inhibitor in the solution and high temperature cause a particularly strong rise of the f-value, that is to say a particularly strong displacement of the saccharase/amylase inhibition relation towards saccharase-inhibition. FIGS. 2 and 3 show the time course of the saccharase/amylase inhibition relation against the hydrolysis time under various hydrolysis conditions. In both FIGS. 2 and 3 the x-axis shows the time in minutes and the y-axis shows the quotient $f$.

FIG. 2 shows the course of the hydrolysis at 100°C.

| Curve 1 | 1 N HCl    | 20 mg/ml,  | Curve 4 | 0.75 | N HCl | 200 mg/ml, |
| Curve 2 | 1 N HCl    | 200 mg/ml, | Curve 5 | 0.5  | N HCl | 20 mg/ml,  |
| Curve 3 | 0.75 N HCl | 20 mg/ml,  | Curve 6 | 0.5  | N HCl | 200 mg/ml, |

FIG. 3 shows the influence of the acid concentration and hydrolysis temperature on the SIU/AIU ratio. C = 20 mg of amylase inhibitor from Strain CBS 961.70 ml of acid (HCl).

| Curve 1 | 2 N 90°C | Curve 5 | 0.5 N 90°C |
| Curve 2 | 2 N 80°C | Curve 6 | 2 N 70°C≅0.5 80°C |
| Curve 3 | 1 N 90°C | Curve 7 | 2 N 60°C |
| Curve 4 | 1 N 80°C | Curve 8 | 1 N 70°C |

The saccharase-inhibiting principle from the hydrolysate produced in the process of the invention is best isolated by adsorption on active charcoal after prior neutralization of the hydrolysate, and subsequent fractional desorption of the inhibitor from the charcoal with aqueous alcohols or aqueous acetone. If the hydrolysate is very dark in color, it can be decolorized with active charcoal before the adsorption of the saccharase inhibitor on the charcoal at acid pH values (pH 1 – 3).

Using the process of the invention samples of saccharase inhibitor having activities up to 15,000 SIU/gram have been produced.

The hydrolytic degradation according to the invention can also take place enzymatically, for which beta-amylase is particularly suitable.

It is known that in animals and man, after intake of foodstuffs and beverages containing saccharose, hyperglycaemias arise which are brought about as a result of a rapid splitting of the saccharose by saccharases of the digestive tract according to the following equation:

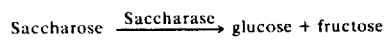

Saccharose $\xrightarrow{\text{Saccharase}}$ glucose + fructose

These hyperglycaemias are particularly strong and of long-lasting pronounced character in the case of diabetics. In the case of adipose subjects the alimentary hyperglycaemia frequently causes a particularly intense insulin secretion which in turn leads to increased synthesis and decreased degradation of fat.

The saccharase inhibitors which have been obtained and isolated in accordance with the above methods, according to the invention, reduce the alimentary hyperglycaemia and hyperinsulinaemia of rats, after treatment with saccharose, considerably.

It is furthermore known that caries occurs particularly strongly and frequently after consumption of beverages and food-stuffs containing saccharose (for example, W. Gold: Advances in Applied Microbiology 11, (1969) 135 – 157). An inhibition of the splitting of saccharose by the inhibitor according to the invention reduces the formation of cariogenic substances in the mouth cavity.

The inhibitors according to the invention are therefore suitable for use as a therapeutic agent for the following indications: adiposity, hyperlipaemia (atherosclerosis), diabetes, pre-diabetes and caries.

The present invention therefore also includes a pharmaceutical composition containing as an active ingredient the saccharase inhibitor produced by the method of this invention, in admixture with a solid or semi-liquid diluent.

Examples of such diluents include: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate (e) agents for retarding dissolution, e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The inhibitor may also be added to foodstuffs and beverages containing saccharose.

Particular examples of the pharmaceutical compositions of this invention are suspensions, granules, chewing gum, toothpaste, mouthwash, foodstuffs and beverages containing the saccharase inhibitor.

The saccharase inhibitor produced by the method of this invention is generally to be administered orally in amounts of 100–10000 SIU/kg body weight per therapeutic administration, which will be once or several times daily before, during or after meals.

The invention further provides medicaments in dosage unit form containing saccharase inhibitor produced by the method of the invention.

The term "medicament in dosage unit form" as used here means physically discrete coherent portions suitable for medical administration, each containing a predetermined individual quantity of the inhibitor, the said quantity being such that one portion is required for a single therapeutic administration in accordance with guidelines set forth above. Examples of such medicaments in dosage unit form according to the invention are tablets, dragees, capsules, sticks of chewing gum and ampoules containing the inhibitor.

Throughout this specification the abbreviation "CBS" refers to microbial strains that have been deposited at the Centraalbureau voor Schimmelcultures, Baarn, Netherlands, under the stated accession number.

EXAMPLE 1

5 g of the amylase inhibitor from the Actinoplanaceae Strain CBS No. 961.70 containing $10 \times 10^6$ AIU/g and 220 SIU/g were dissolved in 50 ml of 0.05 M Na acetate buffer of pH 4.5, 25 mg of beta-amylase from barley were added and the mixture was incubated at 35°C. The splitting was complete after 3 hours. The incubation batch was directly added dropwise to 450 ml of dry spirit while stirring and the white flocculent precipitate was filtered off, washed twice with ethanol and twice with ether and dried in vacuo. Yield: 2.5 g containing $4.6 \times 10^6$ AIU/g and 700 SIU/g.

EXAMPLE 2

100 g of the amylase inhibitor from Stain CBS 961.70 were dissolved in 500 ml of 2 N $H_2SO_4$ and hydrolyzed for 4 hours at 100°C. After cooling, the black-brown solution was adjusted to pH 2.0 with 10 N KOH and was decolorized by treating it twice with 4 g of active charcoal at a time and in each case stirring for about 10 minutes and filtering off. The charcoal was discarded and the light yellow-colored filtrate was neutralized with 10 N KOH (pH 6.6). 20 g of active charcoal were added to adsorb the inhibiting fragments on the charcoal. After stirring for 10 minutes the mixture was filtered and the filtrate was again adsorbed on 10 g of active charcoal. The charcoal residues were combined and the filtrate was discarded. To remove residual salts and glucose, the combined charcoal residues were washed on the filter with 2 liters of distilled water and 2 liters of 2.5% strength ethanol and were subsequently desorbed three times, in each case with 750 ml of 10% strength ethanol and then 15% strength ethanol. For desorption, the mixture was in each case stirred for 10 minutes and the charcoal was then filtered off and treated with fresh desorption agent. The corresponding filtrates from the 10% and 15% desorption were combined, concentrated to approximately 20 ml on a rotary evaporator and subsequently lyophilized. Yield: approximately 2 g of the 10% fraction and 1.2 g of the 15% fraction. Specific activity: 10% fraction 9,000 SIU/g; $0.2 \times 10^6$ AIU/g; 15% fraction 15,000 SIU/g; $0.5 \times 10^6$ AIU/g.

EXAMPLE 3

200 mg of an amylase inhibitor ($6 \times 10^6$ AIU/g, 160 SIU/g) produced by the Actinoplanaceae Strain CBS 615.71 were dissolved in 10 ml of 0.75 N HCl. The starting solution had an activity of $120 \times 10^6$ AIU/liter with 3,200 SIU/liter. This solution was incubated in a water bath at 100°C for 30 minutes and then cooled and tested. The content of amylase inhibitor in the hydrolysate thus obtained was $8 \times 10^6$ AIU/liter and the content of saccharase inhibitor was 21,000 SIU/liter.

EXAMPLE 4

200 mg of an amylase inhibitor ($4 \times 10^6$ AIU/g, 310 SIU/g) produced by the Actinoplanaceae Strain CBS 957.70 were dissolved in 10 ml of 0.75 N HCl. The starting solution had an activity of $80 \times 10^6$ AIU liter and 6,200 SIU/liter. This solution was incubated for 30 minutes in a water bath at 100°C and then cooled and tested. The content of amylase inhibitor in the hydrolysate thus obtained was $10 \times 10^6$ AIU/liter and the content of saccharase inhibitor was 28,000 SIU/liter.

EXAMPLE 5

(Experimental arrangement for demonstrating the action of the active substance from Example 2 on rats in the saccharose exposure test)

To produce a hyperglycaemia and hyperinsulinaemia after feeding with carbohydrate, rats ($n = 6$) receive 2.5 g/kg of saccharose as an orally administered solution. The active substance mentioned is administered orally, additionally to the saccharose, to an equal number of rats in order to weaken the hyperglycaemia and hyperinsulinaemia. The blood glucose and serum insulin are determined at the indicated time intervals after exposure to carbohydrate. Reducing carbohydrates are determined in an auto-analyzer [Technicon, according to Hoffman: J. biol. Chem. 120, 51 (1937)] and the insulin is determined according to Hales and Randle [Biochem. J. 88, 137, (1963)]. Blood is taken from the retro-orbital venous plexus of the rats.

TABLE 1

|  | Blood glucose | | Serum insulin | |
| --- | --- | --- | --- | --- |
| Dose/kg | 10 | 20 min. | 10 | 20 min. |
| Control without saccharose | 79 ± 5.9 | 79 ± 4.8 | 17 ± 11.0 | 9 ± 7.3 |
| Control with saccharose | 142 ± 20 | 148 ± 17 | 31 ± 14.2 | 39 ± 13.2 |
| Saccharose + 100 SIU | 95 ± 5.3[1] | 94 ± 6.3[1] | 8 ± 5.7[2] | 7 ± 2.8[1] |
| Saccharose + 1,000 SIU | 83 ± 5.2[1] | 85 ± 7.6[1] | 11 ± 6.0[3] | 8 ± 5.4[1] |

[1] $P < 0.001$ against saccharose control
[2] $P < 0.01$ against saccharose control
[3] $P < 0.05$ against saccharose control In the above table, blood glucose in mg % (average value ± 1s) and serum insulin in U/ml (average value ± 1s) of fasting rats at various times (expressed in minutes) after oral administration of saccharose ± active substance from Example 2, 15% fraction.

What is claimed is:

1. A pharmaceutical composition comprising as an active ingredient a therapeutically effective quantity of a saccharase inhibitor mixed with a pharmaceutical diluent, wherein said saccharase inhibitor is produced by a process which comprises subjecting to hydrolytic degradation a polysaccharidic or oligosaccharidic amylase inhibitor derived from microorganisms of the order Actinomycetales.

2. A pharmaceutical composition in accordance with claim 1 wherein said amylase inhibitor is produced microbiologically from Actinoplanaceae.

3. A pharmaceutical composition in accordance with claim 1 wherein said amylase inhibitor is produced microbiologically from Strain CBS 961.70.

4. A pharmaceutical composition in accordance with claim 1 wherein said amylase inhibitor is produced microbiologically from Strain CBS 615.71.

5. A pharmaceutical composition in accordance with claim 1 wherein said amylase inhibitor is produced microbiologically from Strain CBS 614.71.

6. A pharmaceutical composition in accordance with claim 1 wherein said amylase inhibitor is produced microbiologically from Strain CBS 957.70.

* * * * *

UNITED STATES PATENT OFFICE
CERTIFICATE OF CORRECTION

Patent No. 3,934,006            Dated January 20, 1976

Inventor(s) Werner Frommer et al

It is certified that error appears in the above-identified patent and that said Letters Patent are hereby corrected as shown below:

Column 1, line 64, "15°14 60°C" should be --15°-60°C--.

Column 5, line 61, after "with" insert --the--.

Column 6, line 18, "Stain" should be --Strain--.

Signed and Sealed this

Sixth Day of July 1976

[SEAL]

Attest:

RUTH C. MASON
*Attesting Officer*

C. MARSHALL DANN
*Commissioner of Patents and Trademarks*